United States Patent [19]

Schohe-Loop et al.

[11] Patent Number: 5,866,562
[45] Date of Patent: Feb. 2, 1999

[54] RING-BRIDGED BIS-QUINOLINES

[75] Inventors: Rudolf Schohe-Loop, Wuppertal; Peter-Rudolf Seidel, Köln; William Bullock, Wuppertal; Achim Feurer, Odenthal; Georg Terstappen, Düsseldorf; Joachim Schuhmacher, Wuppertal; Franz-Josef van der Staay, Lohmar/Wahlscheid; Bernard Schmidt, Lindlar, all of Germany; Richard J. Fanelli, Madison, Conn.; Jane C. Chisholm, Clinton, Conn.; Richard T. McCarthy, Madison, Conn.

[73] Assignee: Bayer Aktiengesellschaft, Leverkusen, Germany

[21] Appl. No.: 738,123

[22] Filed: Oct. 25, 1996

[51] Int. Cl.$^6$ ............ C07D 215/42; C07D 243/08; A61K 31/47

[52] U.S. Cl. ............ 514/183; 514/218; 514/255; 514/313; 540/470; 540/575; 544/363; 546/159

[58] Field of Search ............ 544/363; 546/159; 540/575, 553, 470; 514/183, 218, 255, 313

[56] References Cited

U.S. PATENT DOCUMENTS

| | | | |
|---|---|---|---|
| 3,026,322 | 3/1962 | Schock | 260/286 |
| 3,362,875 | 1/1968 | Strauss et al. | 167/58 |
| 3,974,279 | 8/1976 | Geiszler | 424/258 |

FOREIGN PATENT DOCUMENTS

| | | |
|---|---|---|
| 1 246 733 | 9/1971 | United Kingdom . |
| WO 93/07126 | 4/1993 | WIPO . |
| WO 95/35287 | 12/1995 | WIPO . |

OTHER PUBLICATIONS

Sidorin et al., Beilstein Reg. No. 6361781, Pharm. Chem. J. (Engl. Transl.), 26, 9–10, pp. 704–706, 1992.
Meyer, Beilstein Reg. No. 351978 and 351789, C. R. Hebd. Seances Acad. Sci., 205 (1937) 148, 150, 1937.
Kermack, Beilstein Reg. No. 345676, J. Chem. Soc. 1930 1356, 1360, 1930.
Singh, et al., J. Med. Chem., 14(4), pp. 283–286, 1971.
Damasio et al., Alzheimer's Disease and Related Dementias, Cecil Textbook of Medicine, 20th ed., vol. 2, pp. 1992–1996, 1996.
Gauthier et al., CA 105: 164484, 1986.
Kennerstrom et al., J.Med.Chem.35(11), 1992, 2129–34.
Singh et al., Chem.Pharm.Bull. 23(8), 1975, 1869–73.
Sinha et al., J.Med.Chem. 20(11), 1977, 1528–31.
Deshpande et al., Agricultural and Biological Chemistry, vol. 35, 1971, 1,119–21.
McFayden et al., FEBS Lett. 228(2), 1988, 235–40.
Ferguson et al., Mutat.Res. 232(2), 1990, 337–43.
Galankis et al., J.Med.Chem., 1996, 39, 359–370.
Strekowski et al., J.Org.Chem. 59, 1994, 5886–90.
Singh et al., J.Med.Chem. 14(4), 1971, 283–286.
Haberman et al., "Bee Venom Neurotoxin (Apamin): Iodine Labeling and Characterization of Binding Sites," Eur.J.Biochem. 94, 355–364 (1979).
Mourre et al., "Quantitative Autoradiographic Mapping in Rat Brain of the Receptor of Apamin, a Polypeptide Toxin Specific for One Class of $Ca^{2+}$–Dependent $K^+$Channels," Brain Research, 382, 239–249 (1986).
Heurteaux et al., "Memory processing and a pamin induce immediate early gene expression in mouse brain," Molecular Brain Research, 3, 17–22 (1993).
Messier et al., "Effect of apamin, a toxin that inhibits $Ca^{2+}$–dependent $K^+$channels, on learning and memory processes, " Brain Research, 551, 322–326 (1991).
Behrens et al., "Possible Role of Apamin–Sensitive $K^+$Channels in Myotonic Dystrophy," Muscle & Nerve, 1264–1270 (1994).
Porsolt et al., "Depression: a new animal model sensitive to antidepressant treatments," Nature, 266, 730–732 (1977).
Morris, "Developments of a water–maze procedure for studying spatial learning in the rat," Journal o Neuroscience Methods, 11, 47–60 (1984).

*Primary Examiner*—Mukund J. Shah
*Assistant Examiner*—Deeppak Rao
*Attorney, Agent, or Firm*—Sprung Kramer Schaefer & Briscoe

[57] ABSTRACT

The present invention relates to ring-bridged bis-quinolines of the general formula (I):

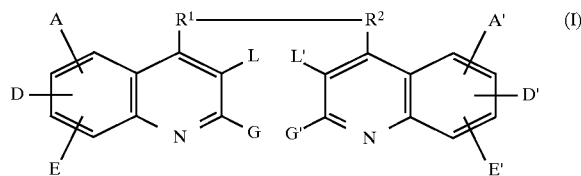

in which the indicated substituents are as defined in the description.

The invention also provides a process for the preparation of compounds of the formula (I), their use for the preparation of drugs, and drugs containing said compounds.

6 Claims, No Drawings

RING-BRIDGED BIS-QUINOLINES

The present invention relates to novel ring-bridged bis-quinolines, to processes for their preparation and to their use in drugs, especially as agents acting on the brain.

It is already known that N,N-bis-(7-chloroquinolin-4-yl)-alkanediamines are used as antimalarial drugs [cf. WO 95/35287; J. Med. Chem. 35 (11), 1992, 2129–34; J. Med. Chem. 14 (4), 1971, 283–286; Chem. Pharm. Bull. 23 (8), 1975, 1869–73; PCT WO 93/07126].

Also, bis-quinaldines are known as drugs for topical infections and leukaemia, as monofunctional AT-selective DNA-intercalating agents and as antibacterial, antitubercular and antitumoral drugs [cf. J. Med. Chem. 20 (11), 1977, 1528–31; Agricultural and Biological Chemistry Vol. 35, 1971, 1, 119–21; FEBS Lett. 228 (2), 1988, 235–40; GB 12 46 733; U.S. Pat. No. 3 362 875; U.S. Pat. No. 3 974 279; Mutat. Res. 232 (2), 1990, 337–43; U.S. Pat. No. 3 026 322].

The publication J. Med. Chem. 1996, 39, 359–370, describes the synthesis and structure-activity relationship of dequalinium derivatives which are capable of inhibiting dequalinium-sensitive afterhyperpolarization.

The present invention relates to novel ring-bridged bis-quinolines of the general formula (I):

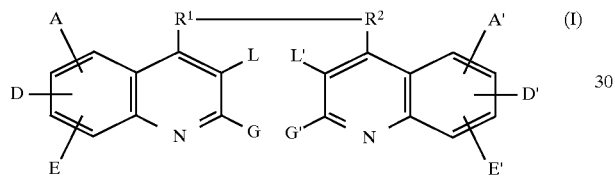

in which

A, A', D, D', E, E', G, G', L and L' are identical or different and are hydrogen, halogen, nitro, trifluoromethyl, cycloalkyl having 3 to 8 carbon atoms, aryl having 6 to 10 carbon atoms, cyano, carboxyl, hydroxyl, linear or branched alkyl, alkoxy or alkoxycarbonyl, each of which has up to 8 carbon atoms, or a group of the formula —(CO)$_a$—NR$^3$R$^4$, wherein a is the number 0 or 1 and R$^3$ and R$^4$ are identical or different and are hydrogen or linear or branched alkyl having up to 7 carbon atoms, and R$^1$ and $^-$R$^2$ together are a radical of the formula

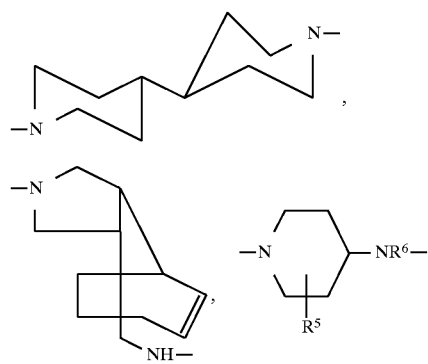

or

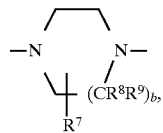

wherein

R$^5$ and R$^7$ are identical or different and are hydrogen, carboxyl, linear or branched alkyl, acyl or alkoxycarbonyl, each of which has up to 6 carbon atoms, or a group of the formula —(CO)$_c$—NR$^{10}$R$^{11}$ or —OR$^{12}$, wherein c is the number 0 or 1, R$^{10}$ and R$^{11}$ are identical or different and are hydrogen, phenyl, benzyl, cycloalkyl having 3 to 6 carbon atoms, carboxyl, hydroxyl, linear or branched acyl or alkoxycarbonyl, each of which has up to 6 carbon atoms, or linear or branched alkyl having up to 6 carbon atoms which is optionally substituted by hydroxyl or by linear or branched alkoxy, acyl or alkoxycarbonyl, each of which has up to 5 carbon atoms, R$^{12}$ is hydrogen or linear or branched alkyl or acyl, each of which has up to 6 carbon atoms, or R$^7$ is linear or branched alkyl having up to 5 carbon atoms which is substituted by a group of the formula —OR$^{13}$, —O—CONR$^{14}$R$^{15}$ or —NR$^{16}$R$^{17}$, wherein R$^{13}$ is as defined above for R$^{12}$ and is identical thereto or different therefrom and R$^{14}$, R$^{15}$, R$^{16}$ and R$^{17}$ are identical or different and are as defined above for R$^{10}$ and R$^{11}$, R$^6$ is hydrogen, phenyl or linear or branched alkyl having up to 4 carbon atoms, b is the number 1, 2 or 3 and R$^8$ and R$^9$ are hydrogen or R$^8$ is hydrogen and R$^9$ is as defined above for R$_5$ and R$^7$ and is identical thereto or different therefrom, and their salts.

Biocompatible salts are preferred within the framework of the present invention. Biocompatible salts of the novel ring-bridged bis-quinolines can be salts of the substances according to the invention with mineral acids, carboxylic acids or sulfonic acids. Examples of particularly preferred salts are those with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

The compounds according to the invention can be present in different stereoisomeric forms within the framework of the present invention. The compounds according to the invention exist in stereoisomeric forms which either behave as image and mirror image (enantiomers) or do not behave as image and mirror image (diastereoisomers). The invention relates both to the antipodes and to the racemic forms and the diastereoisomeric mixtures. The racemic forms and the diastereoisomers can be resolved in a known manner into the stereoisomerically pure components.

Preferred compounds of the general formula (I) according to the invention are those in which A, A', D, D', E, E', G, G', L and L' are identical or different and are hydrogen, fluorine, chlorine, bromine, nitro, trifluoromethyl, cyclopropyl, cyclobutyl, cyclopentyl, cyclohexyl, phenyl, hydroxy, linear or branched alkyl, alkoxy or alkoxycarbonyl, each of which has up to 7 carbon atoms, or a group of the formula —(CO)$_a$—NR$^3$R$^4$,
wherein
a is the number 0 or 1,
R$^3$ and R$^4$ are identical or different and are hydrogen or linear or branched alkyl having up to 6 carbon atoms,
R$^1$ and R$^2$ together are a radical of the formula

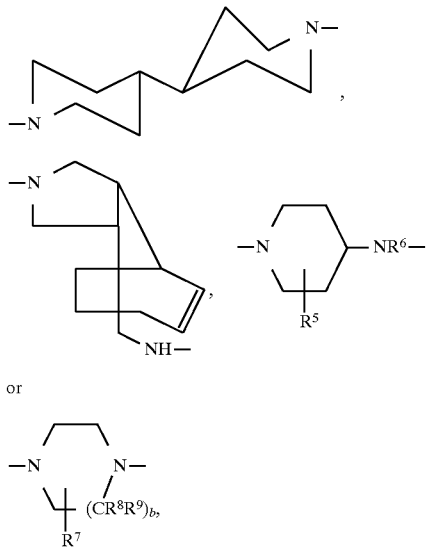

or wherein
R$^5$ and R$^7$ are identical or different and are hydrogen, carboxyl, linear or branched alkyl, acyl or alkoxycarbonyl, each of which has up to 4 carbon atoms, or a group of the formula —(CO)$_c$—NR$^{10}$R$^{11}$ or —OR$^{12}$,
wherein
c is the number 0 or 1,
R$^{10}$ and R$^{11}$ are identical or different and are hydrogen, phenyl, cyclopropyl, cyclopentyl, cyclohexyl, carboxyl, hydroxyl, linear or branched acyl or alkoxycarbonyl, each of which has up to 4 carbon atoms, or linear or branched alkyl having up to 4 carbon atoms which is optionally substituted by hydroxyl or by linear or branched alkoxy, acyl or alkoxycarbonyl, each of which has up to 3 carbon atoms,
R$^{12}$ is hydrogen or linear or branched alkyl or acyl, each of which has up to 4 carbon atoms, or
R$^7$ is linear or branched alkyl having up to 4 carbon atoms which is substituted by a group of the formula —OR$^{13}$, —O—CONR$^{14}$R$^{15}$ or —NR$^{16}$R$^{17}$,
wherein
R$^{13}$ is as defined above for R$^{12}$ and is identical thereto or different therefrom and
R$^{14}$, R$^{15}$, R$^{16}$ and R$^{17}$ are identical or different and are as defined above for R$^{10}$ and R$^{11}$,
R$^6$ is hydrogen, phenyl or linear or branched alkyl having up to 3 carbon atoms,
b is the number 1, 2 or 3 and
R$^8$ and R$^9$ are hydrogen or
R$^8$ is hydrogen and
R$^9$ is as defined above for R$^5$ and R$^7$ and is identical thereto or different therefrom, and their salts.

Particularly preferred compounds of the general formula (I) according to the invention are those in which
A, A', D, D', E, E', G, G', L and L' are identical or different and are hydrogen, cyclopropyl, cyclopentyl, cyclobutyl, cyclohexyl, phenyl, hydroxyl, fluorine, chlorine, trifluoromethyl, nitro, linear or branched alkyl or alkoxy, each of which has up to 4 carbon atoms, or a group of the formula —(CO)$_a$—NR$^3$R$^4$,
wherein
a is the number 0 or 1 and
R$^3$ and R$^4$ are identical or different and are hydrogen or linear or branched alkyl having up to 4 carbon atoms,
R$^1$ and R$^2$ together are a radical of the formula

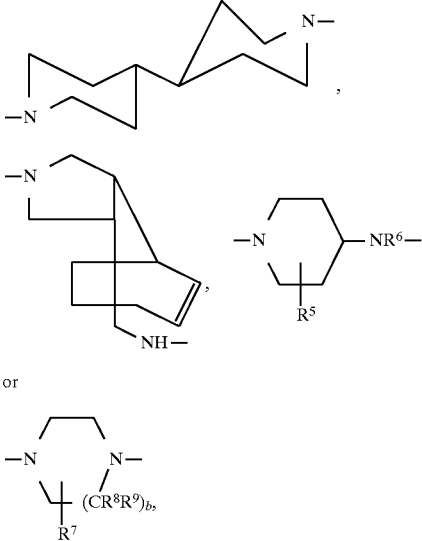

or wherein
R$^5$ and R$^7$ are identical or different and are hydrogen, carboxyl, linear or branched alkyl, acyl or alkoxycarbonyl, each of which has up to 3 carbon atoms, or a group of the formula —(CO)$_c$—NR$^{10}$R$^{11}$ or —OR$^{12}$,
wherein
c is the number 0 or 1,
R$^{10}$ and R$^{11}$ are identical or different and are hydrogen, phenyl, cyclopentyl, cyclohexyl, carboxyl, hydroxyl, linear or branched acyl or alkoxycarbonyl, each of which has up to 3 carbon atoms, or linear or branched alkyl having up to 3 carbon atoms which is optionally substituted by hydroxyl or by linear or branched alkoxy, acyl or alkoxycarbonyl, each of which has up to 3 carbon atoms, and
R$^{12}$ is hydrogen or linear or branched alkyl or acyl, each of which has up to 3 carbon atoms, or
R$^7$ is linear or branched alkyl having up to 3 carbon atoms which is substituted by a group of the formula —OR$^{13}$, —O—CO—NR$^{14}$R$^{15}$ or —NR$^{16}$R$^{17}$,
wherein
R$^{13}$ is as defined above for R$^{12}$ and is identical thereto or different therefrom and
R$^{14}$, R$^{15}$, R$^{16}$ and R$^{17}$ are identical or different and are as defined above for R$^{10}$ and R$^{11}$,
R$^6$ is hydrogen or methyl,
b is the number 1, 2 or 3
R$^8$ and R$^9$ are hydrogen or $R^8$ is hydrogen and $R^9$ is as defined above for $R^5$ and $R^7$ and is identical thereto or different therefrom, and their salts.

A process for the preparation of the compounds of the general formula (I) according to the invention has also been found, said process being characterized in that

[A] 2 equivalents of the compounds of the general formula (II):

![Formula II structure]

(II)

in which

A, D, E, G and L are as defined above and

Y is halogen, preferably fluorine, chlorine or bromine, are reacted with 1 equivalent of the compounds of the general formula (III):

H—R$^1$—R$^2$—H          (III)

in which

R$^1$ and R$^2$ are as defined above, optionally in inert solvents and optionally in the presence of a base, and optionally in the presence of a iodine salt.

[B] 1 equivalent of the compound of the general formula (II) is reacted in excess with the compounds of the general formula (III), under the conditions of process [A], to give compounds of the general formula (IV):

![Formula IV structure]

(IV)

in which

A, D, E, G, L, R$^1$ and R$^2$ are as defined above, and these are then reacted with compounds of the general formula (IIa):

![Formula IIa structure]

(IIa)

in which

A', D', E', G', L' and Y' are as defined for A, D, E, G, L and Y.

The process according to the invention can be exemplified by the following equation:

[A]

![Reaction scheme showing 4-chloroquinoline + piperazine-type diamine → bis-quinolinyl product with N—(CH$_2$)$_2$—N linker]

Suitable solvents are the conventional solvents which are not affected by the reaction conditions. These preferably include alcohols such as methanol, ethanol, propanol, isopropanol, hexanol, octanol or phenol, ethers such as diethyl ether, dioxane, tetrahydrofluran, glycol dimethyl ether or butyl methyl ether, ketones such as acetone or butanone, amides such as N-methylpyrrolidone, dimethylformamide or N-methylphosphorotriamide, dimethyl sulfoxide, acetonitrile, butyronitrile, ethyl acetate, halogenated hydrocarbons such as methylene chloride, chloroform or carbon tetrachloride, pyridine, picoline or N-methylpiperidine. It is also possible to use mixtures of said solvents. Butyronitrile, methylene chloride, phenol and N-methylpyrrolidone are preferred. The reaction can also be carried out without a solvent.

Suitable bases are the conventional inorganic or organic bases. These preferably include alkali metal carbonates such as sodium or potassium carbonate, or organic amines such as diethylamine, triethylamine, tripropylamine, pyridine, picoline, N-methylpiperidine, lutidine or diisopropylethylamine. Diisopropylethylamine and tripropylamine are preferred.

Suitable iodine salts are alkali metal iodides such as lithium iodide, sodium iodide, potassium iodide and caesium iodide, and tetralkylammonium iodides such as benzyltributylammonium iodide. It is preferable to use sodium iodide and potassium iodide.

The iodine salts are generally used in an amount of 0.001 to 1 mol, based on 1 mol of the compounds of the general formula (II).

The base is used here in an amount of 0.8 to 5 mol, preferably of 0.8 to 2 mol, based on 1 mol of the compounds of the general formula (II).

The reactions are generally carried out in the temperature range between −20° C. and the reflux temperature of the solvent, preferably between +20° C. and the reflux temperature of the solvent.

The reaction can be carried out at normal, elevated or reduced pressure (e.g. 0.5 to 5 bar). It is generally carried out at normal pressure.

Some of the compounds of the general formula (II) are known or they can be prepared by known methods, for example by reacting 2-trifluoromethylaniline with ketones [cf. J. Org. Chem. 59, 1994, 5886].

The compounds of the general formula (III) are known per se or can be prepared by conventional methods.

The compounds of the general formulae (IV) and (IVa) are known or novel and can then be prepared as described above.

The compounds according to the invention possess a valuable pharmacological spectrum of action which could not be anticipated.

The compounds according to the invention are ligands for apamine-sensitive potassium channels. This can be shown by studying the affinity for apamine binding sites, e.g. in bovine cerebral membranes. The compounds according to the invention inhibit the ion flows through these channels, as can be shown by rubidium efflux experiments and with electrophysiological methods.

The compounds have a positive influence on learning and memory faculties, as demonstrated by their performance-enhancing action in typical learning and memory models like the water maze, the Morris maze, passive avoidance or reminiscence tests in automated Skinner boxes. They possess an antidepressant potential, as verified by their activity in the Porsolt rat swimming test.

The compounds according to the invention are also suitable for the treatment of myotonic dystrophy, alcoholism and other addiction diseases, sleep disturbances and bronchial asthma.

By virtue of their pharmacological properties, the compounds according to the invention can be used for the preparation of drugs for the treatment of degenerative diseases of the central nervous system, e.g. those occurring in cases of dementia (multi-infarct dementia, MID, primary degenerative dementia, PDD, presenile Alzheimer's disease, HIV dementia and other forms of dementia).

They are also suitable for the treatment of age-related cerebral faculty impairment, organic brain syndrome (OBS) and age-associated memory impairment (AAMI).

They are suitable for the treatment of depression and mania.

1) Binding of $^{125}$I-apamine to bovine cerebral membranes

Calfbrains were obtained from the local abattoir. The hippocampus was prepared on ice and a membrane suspension was made up by homogenization twice in buffer (100 mM Tris-HCl, KCl 5 mM, pH 7.4) and centrifugation at 43,000×g. In a total volume of 500 µl, the incubation mixture contained 200 µg of membrane protein, 30 pM $^{125}$I-apamine and test substances in the concentration range $1\times10^{-9}$ to $1\times10^{-4}$M. The non-specific binding of $^{125}$I-apamine was determined in the presence of $1\times10^{-7}$M unlabelled apamine.

After preincubation for 30 min at room temperature (test substances and membrane homogenate), the samples were placed on ice for 10 min before the radioligand was added. The main incubation time was 60 min on ice. When the reaction time had elapsed, an excess of ice-cooled incubation buffer was added to each sample and the mixture was filtered with suction through cellulose acetate/nitrate membrane filters. The amount of bound $^{125}$I-apamine was measured with a gamma counter.

TABLE A

| Ex. no. | $K_i$ (nmol/l) |
|---|---|
| 12 | 35 |
| 1 | 780 |

Thus the compounds show an unexpectedly high affinity for apamine receptors in the calf brain.

2) Non-radioactive Rb$^+$ efflux assay for the identification of potassium channel modulators The potassium in PC12 cells is exchanged with rubidium, which is not present in the cells. This exchange is performed by incubating the cells over a period of 4 h in a physiological buffer containing 5.4 mM RbCl without KCl. This rubidium subsequently serves as a tracer for potassium.

The cells laden with Rb$^+$ in this way are washed three times and then stimulated by depolarization with 50 mM KCl to open potassium channels (10 min), causing Rb$^+$ to flow out of the cells into the supernatant according to the concentration gradient.

The rubidium contents in the cell supernatant and in the residual cells after they have been lysed with 1% Triton X-100 are then determined by means of atomic absorption spectroscopy. The relative proportion of rubidium in the cell supernatant (=Rb$^+$ efflux) is used as a measure of the potassium channel activity.

The effect of substances on the channel activity is measured by co-incubating the test substance over the ten-minute stimulation period and determining its effect on the Rb$^+$ efflux in the manner described above.

TABLE B

| Ex. no. | % inhibition of the Rb efflux at a test concentration of 10 µM |
|---|---|
| 7 | 58 |
| 12 | 73 |

Thus the compounds according to the invention show an unexpectedly high inhibitory activity on the apamine-sensitive rubidium efflux in PC12 cells.

3) Morris maze

Male ICR mice, 6–8 wks old and approx. 22–28 g, were obtained from Harlan Sprague-Dawley, Inc. (Indianapolis, Ind.) and housed 8/cage with ad libitum access to food and water. The behavioural apparatus consisted of a circular galvanized steel tank painted white with a diameter of 76 cm and divided into four equally spaced quadrants, each containing a plastic fitting that allowed for the placement of an escape platform. Prior to the start of the behavioural testing, the maze was filled daily to a depth of 1 cm above the escape platform (25 cm deep), maintained at a temperature of approx 22° C., and was made opaque by the addition of 0.9 kg of powdered milk. Numerous stationary visual cues were present in the testing room. The data were recorded with the Multiple Zone Distance Traveled program of the Video-V analysis system (Columbus Instruments International Corp., Columbus, Ohio). After a 1 week acclimatization to the animal facility, the mice were given a 90 sec free swim, during which no escape platform was present. One to three days later, acquisition training began and consisted of 4 trials on each day for a total of three days (12 total trials), during which no drugs were given. The mice were randomly assigned a goal quadrant in which the escape platform was located. Animals were then placed in the maze (facing away from the center) at one of four equally spaced positions around the perimeter of the maze. The starting position varied for each mouse until they had started from each of the four positions once daily. On each of the training trials, the mice were allowed 120 sec to find the goal platform. If they failed to do so within the allotted time, they were placed on the platform. The intertrial interval was 30 sec, during which time the mouse remained on the platform. On the fourth day, the mice were given a single 30 sec probe trial in which no escape platform was present. Thirty min or 1 hr prior to the start of the probe trial, mice were randomly assigned to groups that were given either drug or vehicle, and the time spent in each quadrant was measured.

The present invention also includes pharmaceutical formulations which contain one or more compounds of the general formula (I) together with inert, non-toxic, pharmaceutically appropriate adjuncts and excipients, or which consist of one or more active substances of the formula (I), as well as processes for the preparation of these formulations.

The active substances of the formula (I) should be present in these formulations in a concentration of 0.1 to 99.5% by weight, preferably of 0.5 to 95% by weight of the total mixture.

In addition to the active substances of the formula (I), the pharmaceutical formulations can also contain other pharmaceutical active substances.

The pharmaceutical formulations mentioned above can be prepared in a conventional manner by known methods, for example with one or more adjuncts or excipients.

To achieve the desired result, it has generally proved advantageous to administer the active substance or substances of the formula (I) in total amounts of about 0.01 to about 100 mg/kg, preferably in total amounts of about 0.01 mg/kg to 10 mg/kg of body weight per 24 hours, optionally in the form of several individual doses.

However, it may be advantageous to deviate from said amounts, depending on the nature and body weight of the subject treated, the individual response to the drug, the nature and severity of the disease, the type of formulation and administration and the time or interval at which the drug is administered.

Starting compounds

EXAMPLE I

Methyl 1,4-dibenzyl-[1,4]-diazepan-6-carboxylate

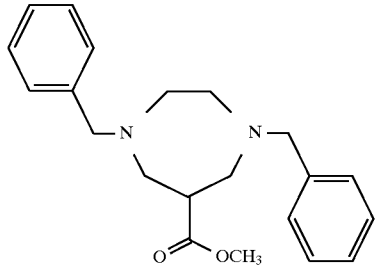

A solution of 8.8 g (34 mmol) of methyl 3-bromo-2-bromomethylpropionate in 80 ml of absolute toluene is added dropwise at room temperature, with stirring, to a solution of 8.0 g (33 mmol) of N,N'-dibenzyl-ethane-1,2-diamine and 6.7 g (66 mmol) of triethylamine in 60 ml of absolute toluene and the mixture is then stirred for 16 hours at 80° to 90° C. After cooling, it is shaken with 200 ml of aqueous sodium carbonate solution and the organic phase is separated off and dried over sodium sulfate. 11 g of a yellow oil are isolated from the toluene solution and this is purified by column chromatography on silica gel (methylene chloride/methanol, 100/2) to give methyl 1,4-dibenzyl-[1,4]-diazepan-6-carboxylate in the form of a light yellow oil.

Yield: 6.0 g (53%)

$R_f$ (silica gel; methylene chloride/methanol, 100/2): 0.23

The following compounds can be obtained analogously to Example I:

EXAMPLE II

Methyl (±)-1,4-dibenzyl-[1,4]-diazepan-2-carboxylate

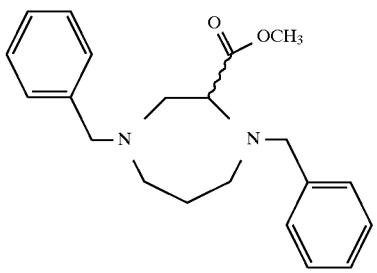

Analogously to the instructions in Example I, 3.7 g (33%) of the title compound are prepared (yellow oil) from 8.4 g (33 mmol) of N,N'-dibenzyl-propane-1,3-diamine and 8.1 g (33 mmol) of methyl (±)-2,3-dibromopropionate in the presence of 6.7 g (66 mmol) of triethylamine.

$R_f$ (silica gel; methylene chloride/methanol, 100/1): 0.18

EXAMPLE III

Methyl (±)-1,4-dibenzyl-[1,4]-diazepan-5-carboxylate

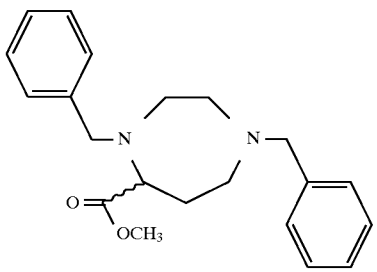

Analogously to the instructions in Example I, 3.7 g (31%) of the title compound are prepared (colorless oil) from 8.4 g (35 mmol) of N,N'-dibenzyl-ethane-1,2-diamine and 9.1 g (35 mmol) of methyl (±)-2,4-dibromobutyrate in the presence of 7.1 g (70 mmol) of triethylamine.

$R_f$ (silica gel; methylene chloride/methanol, 100/3): 0.23

EXAMPLES IV and V 1,4-Dibenzyl-[1,4]-diazepan-6-carboxamide

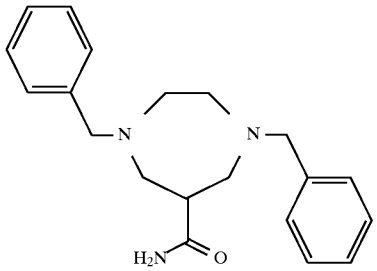

(IV)

Anhydrous ammonia is introduced up to the saturation point, with ice-cooling at 0° to 5° C., into a solution of 6.0 g (18 mmol) of methyl 1,4-dibenzyl-[1,4]-diazepan-6-carboxylate in 200 ml of absolute methanol, to which 0.1 g of potassium cyanide has been added. After the mixture has been standing for 14 days at room temperature, the solvent is evaporated off and the colorless residue is chromatographed on silica gel (methylene chloride/methanol, 100/2) to give the amide in the form of colorless crystals.

M.p.: 76° to 77° C.

Yield: 5.0 g (87%)

1,4-Dibenzyl-[1,4]-diazepan-6-carboxamide dihydrochloride:

(NB: incorrect formula?)

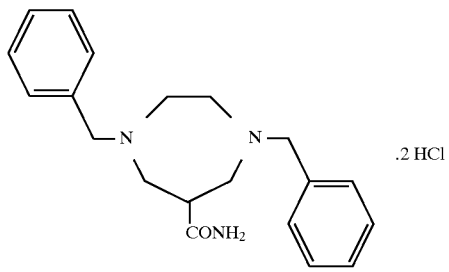
(V)

0.36 g (95%) of the abovementioned compound from 0.31 g (0.96 mmol) of the free base by the addition of HCl/diethyl ether; colorless crystals.

M.p.: 215° C.

The following compounds can be obtained analogously to Examples IV and V:

EXAMPLES VI AND VII (±)-1,4-Dibenzyl-[1,4]-diazepan-2-carboxamide

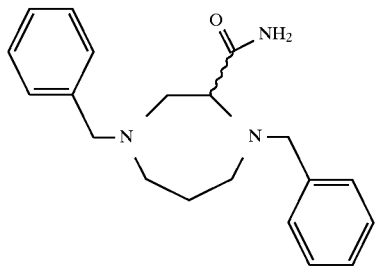
(VI)

Analogously to the instructions in Example IV, 4.9 g (67%) of the title compound are prepared (light yellow oil) from 7.6 g (22 mmol) of methyl (±)-1,4-dibenzyl-[1,4]-diazepan-2-carboxylate.

$R_f$ (silica gel; methylene chloride/methanol, 100/3): 0.34

(±)-1,4-Dibenzyl-[1,4]-diazepan-2-carboxamide dihydrochloride:

(NB: incorrect formula?)

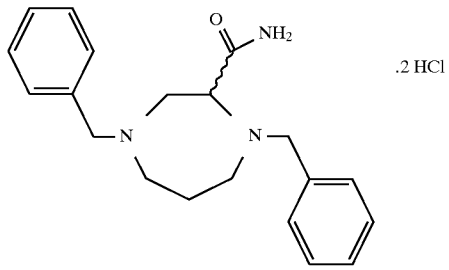
(VII)

Analogously to the instructions in Example IV, 0.26 g (85%) of the title compound is prepared (colorless crystals) from 0.306 g (0.77 mmol) of the free base by the addition of HCl/diethyl ether.

M.p.: 148° C.

EXAMPLES VIII AND IX (±)-1,4-Dibenzyl-[1,4]-diazepan-5-carboxamide

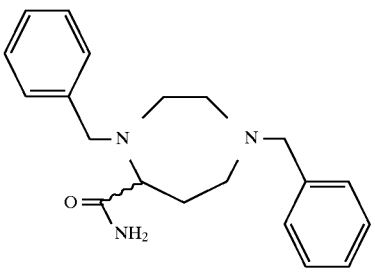
(VIII)

2.1 g (59%) of the title compound are prepared (colorless crystals) from 3.7 g (11 mmol) of methyl (±)-1,4-dibenzyl-[1,4]-diazepan-5-carboxylate.

M.p.: 117° to 118° C.

(±)-1,4-Dibenzyl-[1,4]-diazepan-5-carboxamide dihydrochloride:

(NB: incorrect formula?)

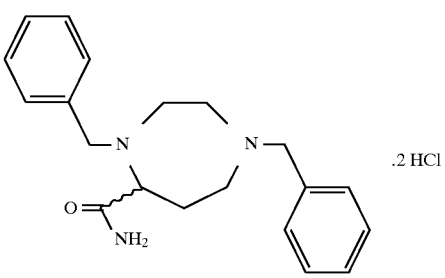
(IX)

Analogously to the instructions in Example V, 0.114 g (97%) of the title compound is prepared (colorless crystals) from 0.118 g (0.3 mmol) of the free base by the addition of HCl/diethyl ether.

M.p.: 195° C.

EXAMPLE X

[1,4]-Diazepan-6-carboxamide

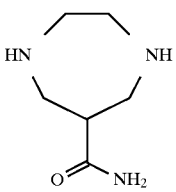

4.3 g (13 mmol) of 1,4-Dibenzyl-[1,4]-diazepan-6-carboxamide are dissolved in 100 ml of methanol and hydrogenated at room temperature and normal pressure for 2.5 hours in the presence of 0.4 g of 10% palladium on activated charcoal. The mixture is filtered on kieselguhr and the filtrate is evaporated to dryness. Treatment of the residue with cyclohexane gives the carboxamide in the form of colorless crystals.

M.p.: 178° to 179° C.;

Yield: 1.88 g (99%)

EXAMPLE XI (±)-[1,4]-Diazepan-2-carboxamide

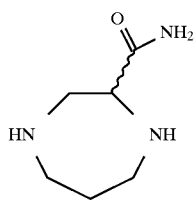

Analogously to the instructions in Example X, 1.9 g (89%) of the title compound are prepared (colorless crystals) from 4.8 g (15 mmol) of (±)-1,4-dibenzyl-[1,4]-diazepan-2-carboxamide.

M.p.: 91° to 92° C.

EXAMPLE XII (±)-[1,4]-Diazepan-5-carboxamide

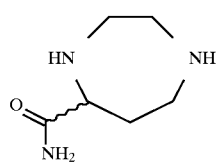

Analogously to the instructions in Example X, 0.8 g (90%) of the title compound is prepared (colorless crystals) from 2.0 g (6.2 mmol) of (±)-1,4-dibenzyl-[1,4]-diazepan-5-carboxamide.

M.p.: 82° C.

EXAMPLES XIII AND XIV (1,4-Dibenzyl-[1,4]-diazepan-6-yl)-methanol

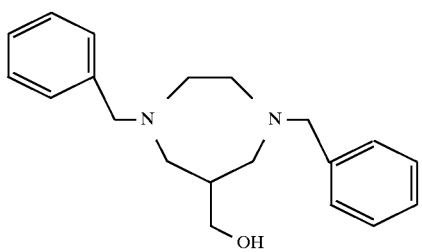

(XIII)

A solution of 30 g (88.6 mmol) of methyl 1,4-dibenzyl-[1,4]-diazepan-6-carboxylate in 125 ml of absolute THF is added dropwise at 5° C. to 125 ml of a 70% toluene solution of sodium bis-(2-methoxyethoxy)-aluminum dihydride which has been diluted with 375 ml of absolute THF. The mixture is subsequently stirred for 4 h at room temperature and then hydrolyzed by the dropwise addition of 70 ml of water. The pH is adjusted to 12 with 1N sodium hydroxide solution and the mixture is extracted with methylene chloride. The organic phase is dried over $Na_2SO_4$ and evaporated under vacuum. The oily residue is purified by chromatography on silica gel (eluent: $CH_2Cl_2/CH_3OH$, 100/5).

Yield: 21 g (76% of theory); light yellow oil

MS (DCI): 311 [M+H]$^+$

Dihydrochloride (XIV): from the amine by precipitation with HCl/diethyl ether; white crystals.

M.p. 110° C.

EXAMPLE XV

[1,4]-Diazepan-6-yl-methanol

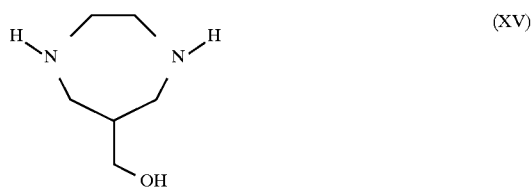

(XV)

2.26 g (7.3 mmol) of (1,4-dibenzyl-[1,4]-diazepan-6-yl)-methanol are dissolved in 150 ml of methanol and hydrogenated at room temperature and normal pressure in the presence of 0.5 g of 10% palladium on activated charcoal. [1,4]-Diazepan-6-yl-methanol is obtained in the form of a light yellow oil by filtration and concentration of the filtrate.

Yield: 0.9 g (95% of theory)

MS (DCI): 131 [M+H]$^+$

EXAMPLES XVI AND XVII 1,4-Dibenzyl-[1,4]-diazepan-6-carboxylic acid diethylamide

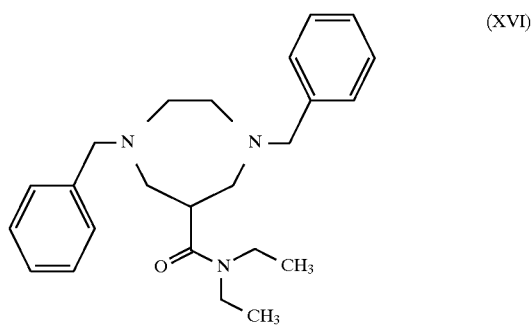

(XVI)

14.25 ml (29 mmol) of a 2 molar solution of $Al(CH_3)_3$ in toluene are diluted with 50 ml of toluene and cooled to −15° C. 3 ml. (2.1 g; 29 mmol) of diethylamine are then added dropwise very slowly under argon as inert gas, with stirring, and the mixture is subsequently stirred for 30 min at −10° C. and warmed to room temperature over 1 h. A solution of 8.5 g (25 mmol) of methyl 1,4-dibenzyl-[1,4]-diazepan-6-carboxylate in 10 ml of toluene is added dropwise to the reaction mixture, which is stirred for 24 h at 80° C. It is allowed to cool, 1N hydrochloric acid is added, with cooling, until a clearly acid reaction is obtained, and the pH is brought to 7.5 by the addition of $NaHCO_3$. The phases are separated and the aqueous phase is extracted with methylene chloride. The combined organic solutions are dried over $Na_2SO_4$ and concentrated under vacuum. The oily residue is purified by chromatography on silica gel (eluent: $CH_2Cl_2/CH_3OH$, 100/5).

Yield: 4.5 g (47% of theory); light yellow oil

MS (DCI): 380 [M+H]$^+$

Dihydrochloride (XVII): 0.19 g (80% of theory) from 0.2 g (0.53 mmol) of the free base by the addition of HCl/diethyl ether; white crystals.

M.p.: 235° C.

EXAMPLES XVIII AND XIX

[1,4]-Diazepan-6-carboxylic acid diethylamide

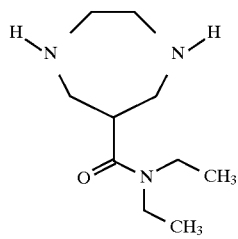
(XVIII)

2.2 g (5.8 mmol) of 1,4-dibenzyl-[1,4]-diazepan-6-carboxylic acid diethylamide are dissolved in 50 ml of ethanol and hydrogenated over 2 h at room temperature and normal pressure in the presence of 0.5 g of 10% palladium on activated charcoal. Filtration over kieselguhr gives an almost colorless filtrate from which [1,4]-diazepan-6-carboxylic acid diethylamide is obtained in the form of a light yellow oil by concentration under vacuum.

Yield: 1.09 g (94% of theory)

MS (DCI): 200 [M+H]$^+$

Dihydrochloride (XIX): from the amine by precipitation with HCl/diethyl ether; white crystals.

M.p.: 190° C.

EXAMPLE XX (1,4-Dibenzyl-[1,4]-diazepan-6-ylmethyl)-diethylamine

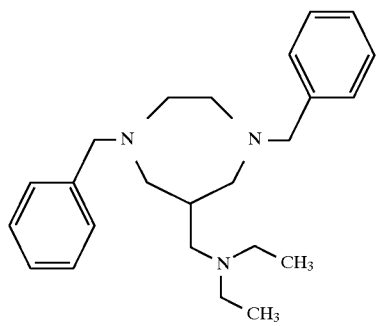
(XX)

8.5 ml of a 70% solution of sodium bis-(2-methoxyethoxy)-aluminum dihydride in toluene are diluted with 20 ml of absolute THF, and a solution of 2.3 g (6.0 mmol) of 1,4-dibenzyl-[1,4]-diazepan-6-carboxylic acid diethylamide in 25 ml of absolute THF is added dropwise at 5° C. under argon as inert gas, with stirring. The mixture is subsequently stirred for 18 h at room temperature, ice-water is added and the mixture is concentrated under vacuum to a final volume of ca. 25 ml. After the addition of 80 ml of water, the mixture is extracted with diethyl ether, the organic phase is dried over Na$_2$SO$_4$ and the solvent is evaporated off.

The oily residue is purified by chromatography on silica gel (eluent: CH$_2$Cl$_2$/CH$_3$OH, 100/5).

Yield: 1.5 g (68% of theory); yellow oil

MS (DCI): 366 [M+H]$^+$

EXAMPLE XXI

[1,4]-Diazepan-6-ylmethyl-diethylamine

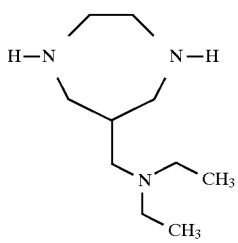
(XXI)

1.0 g (2.7 mmol) of (1,4-dibenzyl-[1,4]-diazepan-6-ylmethyl)-diethylamine in 50 ml of methanol is hydrogenated over 2 h at room temperature in the presence of 0.36 g of 10% palladium on activated charcoal.

Yield: 0.4 g (79% of theory); colorless oil

MS (DCI): 186 [M+H]$^+$

Preparatory Examples

General working instructions for the preparation of the bis-quinolines

The appropriate 4-chloroquinoline derivative (20 mmol) and the diamine (20 mmol) were heated at 160° C. for 16 h under an argon atmosphere. After cooling to room temperature, 50 ml of 1N sodium hydroxide solution and 100 ml of dichloromethane were added and the mixture was stirred until two homogeneous phases had formed. The organic phase was washed with water until the washings were neutral, dried over magnesium sulphate and concentrated to dryness. The product could be separated from the residue by column chromatography on aluminum oxide (ICN, type N, act. I) using dichloromethane/methanol/triethylamine 80/2/1 (unless indicated otherwise in the Tables) as the eluent. The product fractions were concentrated to dryness, taken up with 80 ml of dichloromethane and washed with 1N sodium hydroxide solution (2×30 ml) and water (2×30 ml). The organic phase was dried over magnesium sulphate and concentrated to dryness to give the desired product. Extraction by stirring in a suitable solvent (see the notes in the Tables) was necessary for further purification in some cases.

Yield: 4 to 50%

The bis-quinolines listed in Tables 1 and 2 were prepared by this process.

TABLE 1

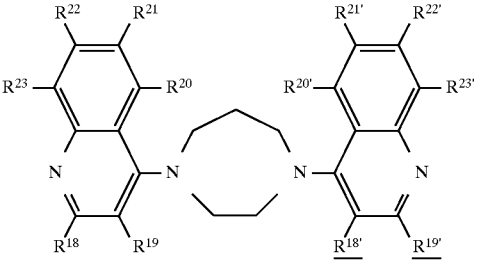

| Bsp. Nr. | $R^{18}/R^{18'}$ | $R^{19}/R^{19'}$ | $R^{20}/R^{20'}$ | $R^{21}/R^{21'}$ | $R^{22}/R^{22'}$ | $R^{23}/R^{23'}$ | Smp. (°C.) $R_f$ Wert[a] |
|---|---|---|---|---|---|---|---|
| 1 | H | H | H | H | H | H | 131 |
| 2 | H | H | H | H | Cl | H | 202 |
| 3 | H | H | H | H | H | $CH_3$ | 128 |
| 4[b] | H | H | H | H | H | $CF_3$ | 208 |
| 5[a] | H | $CH_3$ | H | H | $CH_3$ | $CH_3$ | 200 |
| 6[b] | $CH_3$ | H | H | H | H | H | 138 |
| 7 | $CH_3$ | H | OH | H | H | H | |
| 8 | $CH_3$ | H | Cl | H | H | $CH_3$ | 186 |
| 9 | $CH_3$ | H | H | $NO_2$ | H | H | >250 |
| 10[d] | $CH_3$ | H | H | $OCH_3$ | H | H | 68 |
| 11 | $CH_3$ | H | H | H | $N(CH_3)_2$ | H | 190 |
| 12[d] | $CH_3$ | H | H | H | H | $CH_3$ | 140 |
| 13[d] | $CH_3$ | H | H | H | H | Cl | $R_f = 0{,}77$ |
| 14 | $CH_3$ | H | H | H | H | F | 160 |
| 15[d] | $CH_3$ | H | H | H | H | Cl | $R_f = 0{,}77$ |
| 16[d] | $CF_3$ | H | H | H | H | $CF_3$ | 191 |
| 17[c] | $CF_3$ | H | $NO_2$ | $CH_3$ | H | H | >250 |
| 18 | Et | H | H | H | H | H | 95 |
| 19 | n-Pr | H | H | H | H | H | |
| 20[f] | i-Pr | H | H | H | H | H | $R_f = 0{,}76$ |

| Ex. no. | $R^{18}/R^{18'}$ | $R^{19}/R^{19'}$ | $R^{20}/R^{20'}$ | $R^{21}/R^{21'}$ | $R^{22}/R^{22'}$ | $R^{23}/R^{23'}$ | M.p. (°C.) $R_f$ value |
|---|---|---|---|---|---|---|---|
| 21[f] | t-Bu | H | H | H | H | H | 165 |
| 22 | $CH_3$ | H | H | H | H | $CH(CH_3)_2$ | |
| 23 | $R_{11}$: $CH_3$ $R_{11'}$: $CH(CH_3)_2$ | H | H | H | H | $R_{16}$: H $R_{16'}$: $CH_3$ | |
| 24 | $CH_3$ | H | H | H | H | $R_{16}$: H $R_{16'}$: $CH_3$ | |
| 25 | $CH(CH_3)_2$ | H | H | H | H | $CH_3$ | |
| 26 | $CH_3$ | H | H | H | H | $CH_2CH_3$ | |
| 27 | $CH_3$ | $CH_3$ | H | H | H | H | |
| 28 | $R_{11}$: $CH_3$ $R_{11'}$: $CH(CH_3)_2$ | H | H | H | H | H | |
| 29 | phenyl | H | H | H | H | H | |
| 30 | $CH_3$ | H | H | H | H | phenyl | |
| 31 | $CH_3$ | H | H | $CH(CH_3)_2$ | H | H | |
| 32 | $CH_3$ | H | H | $N(CH_3)_2$ | H | H | |
| 33 | $CH_3$ | H | H | $CH_3$ | H | $CH_3$ | |

[a] thin layer chromatography on precoated aluminium oxide TLC plates using dichloromethane/methanol/triethylamine, 80/2/1
[b] extracted by stirring diethyl ether
[c] extracted by stirring with TBME (tert-butyl methyl ether)
[d] extracted by stirring with n-pentane
[e] chromatography on silica gel 60, 63 to 200 μm, Merck, using toluene/ethyl acetate, 50/1; then extracted by stirring with n-pentane
[f] the compounds were prepared from the appropriate 4-fluoroquinoline derivatives

TABLE 2

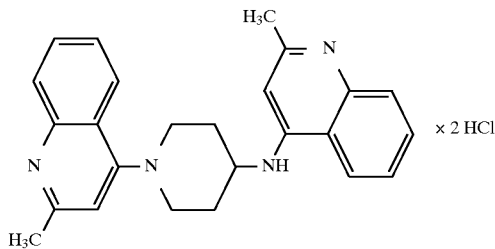

| Ex. no. | G/G' | A/A' | R¹—R² | M.p. (°C.) |
|---|---|---|---|---|
| 34 | CH₃ | H | (structure) | >250 |

EXAMPLE 35

(2-Methyl-quinolin-4-yl)-[1-(2-methyl-quinolin-4-yl)-piperidin-4-yl]-amine dihydrochloride

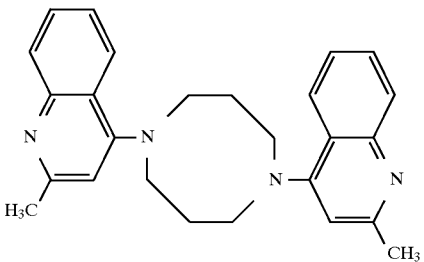

5.3 g (30 mmol) of 4-chloro-2-methyl-quinoline, 3.0 g (30 mmol) of 4-amino-piperidine, 1.4 g (15 mmol) of phenol and 0.174 g of potassium iodide are reacted for 16 hours at 140° C. The melt is cooled, dissolved in methylene chloride and extracted by shaking with 1N sodium hydroxide solution. The organic phase is dried over sodium sulphate, filtered and evaporated. The crude product is subjected to preliminary purification by chromatography on aluminum oxide (toluene/ethanol, 10/1). Subsequent chromatography on silica gel (methylene chloride/methanol, 100/1 to 100/4) gives a pure product in the form of an amorphous resin.

Yield: 2.28 g (20%)

2.6 g of amorphous base are dissolved in methylene chloride and converted to the dihydrochloride by the dropwise addition of 2 equivalents of HCl/diethyl ether; yellowish crystals.

M.p.:>240° C.

Yield: 1.93 g (76%)

EXAMPLE 36

1,4-Bis-(2-methyl-quinolin-4-yl)-[1,5]-diazocane

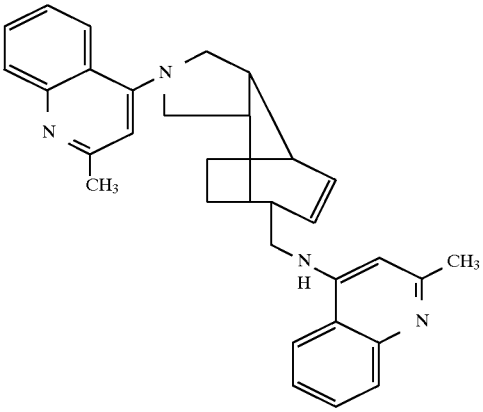

A mixture of 0.05 g (4.4 mmol) of [1,5]-diazocane, 1.56 g (8.8 mmol) of 4-chloro-2-methyl-quinoline and 0.206 g (2.2 mmol) of phenol is heated at 140° C. for 1.5 hours in the presence of 25 mg of potassium iodide. After cooling, the reaction product, a vitreous solid, is dissolved in methanol, the solution is evaporated and the residue is taken up with methylene chloride and subjected to preliminary purification by chromatography on silica gel (elution with methylene chloride/methanol gradients, 100/1 to 10/1). The resulting product (1.26 g) is taken up with methylene chloride and extracted by shaking with a little sodium hydroxide solution (45%). The organic phase is washed with water and dried over sodium sulphate to give 1.09 g of product, which is chromatographed again on silica gel (methylene chloride/methanol/conc. aqueous ammonia solution, 100/4/0.4) for further purification. Distillation of the solvent gives 0.837 g of product, which crystallizes from ethyl acetate.

M.p.: 145° C.

Yield: 0.67 g (38%)

EXAMPLE 37

(2-Methyl-quinolin-4-yl)-[4-(2-methyl-quinolin-4-yl)-4-aza-tricyclo[5.2.2.0$^{2,6}$]-undec-8-en-1-ylmethyl]-amine 16 mg of potassium iodide are added to a mixture of 0.5 g (2.8 mmol) of C-(4-aza-tricyclo[5.2.2.0$^{2,6}$]undec-8-en-1-yl)-methylamine, 0.99 g (5.6 mmol) of 4-chloro-2-methyl-quinoline and 0.132 g (1.3 mmol) of phenol and the resulting mixture is heated at 140° C. for 1 hour. The cooled melt is dissolved in methanol, HCl/diethyl ether is added and the mixture is evaporated. To eliminate the by-products, the mixture of salts is separated on silica gel using methylene chloride/methanol, 100/1 as the eluent. The product obtained from the evaporated eluates is dissolved in diethyl ether and washed with 2N sodium hydroxide solution and water. It is then chromatographed again on silica gel (methylene chloride/methanol/conc. aqueous ammonia solution, 100/1/0.1) to give an amorphous product, which crystallizes from ethyl acetate.

M.p.: 122° to 124° C.;

Yield: 0.46 g (36%)

The solvent is evaporated off to give 1.44 g of product, which is chromatographed twice on silica gel. Eluent: methylene chloride/methanol/conc. aqueous ammonia solution, (1) 100/4/0.4; (2) 100/2/0.2. The eluates are evaporated to isolate 0.99 g of product, which crystallizes from ethyl acetate.

M.p.: 128° C.;

Yield: 0.65 g (29%)

EXAMPLE 38

1,4-Bis-(2-methyl-quinolin-4-yl)-[1,4]-diazepan-6-carboxamide

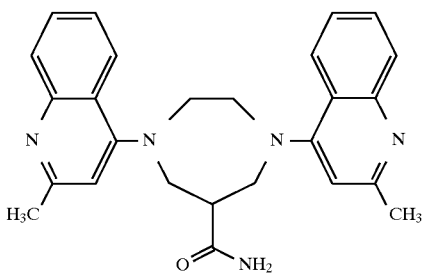

A mixture of 1.06 g (6 mmol) of 4-chloro-2-methyl-quinoline, 0.43 g (3 mmol) of [1,4]-diazepan-6-carboxamide and 0.141 g (1.5 mmol) of phenol is heated at 140° C. for 2 hours in the presence of 18 mg of potassium iodide. After cooling, the reaction product, a vitreous solid, is dissolved in methylene chloride and chromatographed on silica gel; elution with methylene chloride/methanol/conc. aqueous ammonia solution (100/1/0.1) gives the pure title compound in the form of colourless crystals.

M.p.: 225° C.

Yield: 0.024 g (1.9%)

EXAMPLE 39

(±)-1,4-Bis-(2-methyl-quinolin-4-yl)-[1,4]-diazepan-2-carboxamide

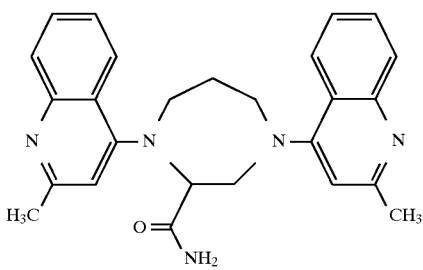

Analogously to the instructions in Example 26, 0.026 g (6.1%) of the title compound is prepared (colourless crystals) from 0.143 g (1 mmol) of (±)-[1,4]-diazepan-2-carboxamide, 0.445 g (2 mmol) of 4-bromo-2-methylquinoline and 0.03 g (0.3 mmol) of phenol over 14.5 hours at 100° C. in the presence of 0.03 g of potassium iodide.

M.p.: 130° to 131° C.;

Yield: 0.88 g (77%)

The compounds listed in Table 3 are prepared analogously to the instructions in Example 39:

TABLE 3

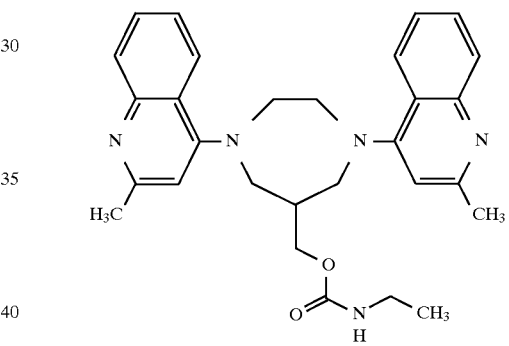

| Example | $R^7$ | M.p./$R_f$ |
|---|---|---|
| 40 | —CH$_2$OH | 195° C. |
| 41 | —CON(C$_2$H$_5$)$_2$ | a) |
| 42 | —OH | 187–189° C. |
| 43 | —CH$_2$N(C$_2$H$_5$)$_2$ | b) | a) MS (FAB): 482 [M + H]$^+$
b) MS (DCI): 468 [M + H]$^+$

EXAMPLE 44

1,4-Bis-(2-methyl-quinolin-4-yl)-[1,4]-diazepan-6-ylmethyl ethylcarbamate

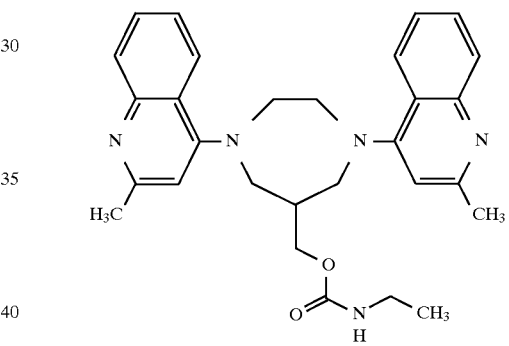

0.345 g (4.9 mmol) of ethyl isocyanate is added, with stirring, to a solution of 0.2 g (0.48 mmol) of 1,4-bis-(2-methyl-quinolin-4-yl)-[1,4]-diazepan-6-yl-methanol in 10 ml of absolute pyridine and the reaction mixture is stirred for 24 h at room temperature. It is then diluted with water and extracted with methylene chloride. The organic phase is washed several times with water, dried over Na$_2$SO$_4$ and concentrated under vacuum. The residue is purified by chromatography on silica gel (eluent: CH$_2$Cl$_2$/CH$_3$OH/NH$_4$OH, 100/2/0.2).

Yield: 0.11 g (47% of theory); amorphous solid

MS (DCI): 484 [M+H]$^+$

We claim:

1. Ring-bridged bis-quinolines of the formula (I)

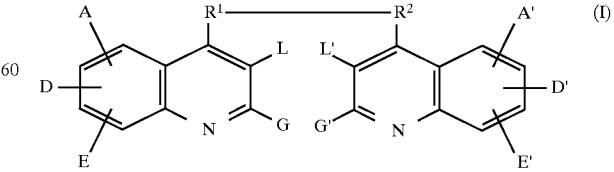

in which

A, A', D, D', E, E', G, G', L and L' are identical or different and are hydrogen, cyclopropyl, cyclopentyl, cyclobutyl, cyclohexyl, phenyl, hydroxyl, fluorine, chlorine, trifluoromethyl, nitro, linear or branched alkyl or alkoxy, each of which has up to 4 carbon atoms, or a group of the formula —(CO)$_a$—NR$^3$R$^4$, wherein a is the number 0 or 1

R$^3$ and R$^4$ are identical or different and are hydrogen or linear or branched alkyl having up to 4 carbon atoms, R$^1$ and R$^2$ together are a radical of the formula

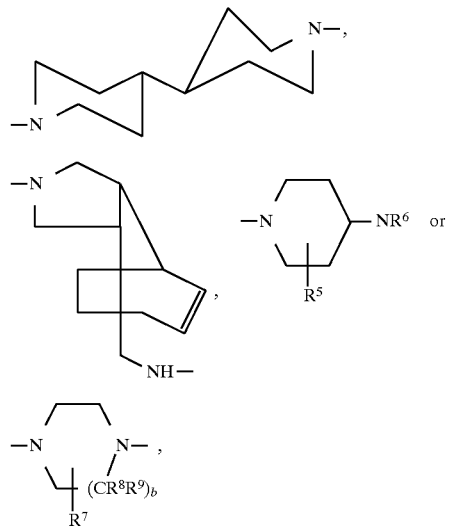

wherein

R$^5$ and R$^7$ are identical or different and are hydrogen, carboxyl, linear or branched alkyl, acyl or alkoxycarbonyl, each of which has up to 3 carbon atoms, or a group of the formula —(CO)$_c$—NR$^{10}$R$^{11}$ or —OR$^{12}$, wherein c is the number 0 or 1, R$^{10}$ and R$^{11}$ are identical or different and are hydrogen, phenyl, cyclopentyl, cyclohexyl, carboxyl, hydroxyl, linear or branched acyl or alkoxycarbonyl, each of which has up to 3 carbon atoms, or linear or branched alkyl having up to 3 carbon atoms which is optionally substituted by hydroxyl or by linear or branched alkoxy, acyl or alkoxycarbonyl, each of which has up to 3 carbon atoms, R$^{12}$ is hydrogen or linear or branched alkyl or acyl, each of which has up to 3 carbon atoms, or R$^7$ is linear or branched alkyl having up to 3 carbon atoms which is substituted by a group of the formula —OR$^{13}$, —O—CO—NR$^{14}$R$^{15}$ or —NR$^{16}$R$^{17}$, wherein R$^{13}$ is as defined above for R$^{12}$ and is identical thereto or different therefrom R$^{14}$, R$^{15}$, R$^{16}$ and R$^{17}$ are identical or different and are as defined above for R$^{10}$ and R$^{11}$, R$^6$ is hydrogen or methyl, b is the number 1, 2 or 3

R$^8$ and R$^9$ are hydrogen or

R$^8$ is hydrogen and

R$^9$ is as defined above for R$^5$ and R$^7$ and is identical thereto or different therefrom, with the proviso that A, A', E, E', L, L', G, and G' are not hydrogen, when D and D' are halogen or trifluoromethyl in positions 7 and 7' of the quinoline rings, and when R$^1$ and R$^2$ together are an unsubstituted piperazine radical and with the proviso that A, A', E, E', L and L' are not hydrogen, when D and D' are methoxy in positions 7 and 7' of the quinoline rings, and when G and G' are methyl, and when R$^1$ and R$^2$ together are an unsubstituted piperazine radical and with the proviso that A, A', E, E', L and L' are not hydrogen, when D and D' are methoxy or methyl in positions 6 and 6' of the quinoline rings, and when G and G' are methyl and when R$^1$ and R$^2$ together are an unsubstituted piperazine radical and with the proviso that A, A', D, D', L, and L' are not hydrogen, when E and E' are methyl or hydrogen in positions 8 and 8' of the quinoline rings, and when G and G' are methyl, and when R$^1$ and R$^2$ together are an unsubstituted piperazine radical, and their salts.

2. 1,4-Bis-(2-methyl-quinolin-4-yl)-[1,4]-diazepane, and 1,4-Bis-(2-isopropyl-quinolin-4-yl)-[1,4]-diazepane.

3. A process for the preparation of ring-bridged bis-quinolines according to claim 1, which comprises

[A] 2 equivalents of the compounds of the general formula (II):

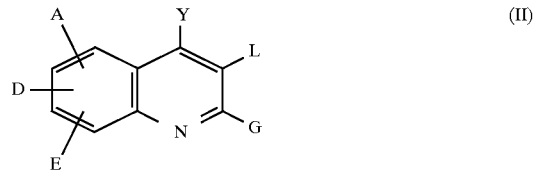

in which

A, D, E, G and L are as defined above and

Y is halogen, fluorine, chlorine or bromine, are reacted with 1 equivalent of the compounds of the general formula (III):

in which

R$^1$ and R$^2$ are as defined above, optionally in inert solvents and optionally in the presence of a base, and optionally in the presence of a iodine salt, or

[B] 1 equivalent of the compound of the general formula (II) is reacted in excess with the compounds of the general formula (III), under the conditions of process [A], to give compounds of the general formula (IV):

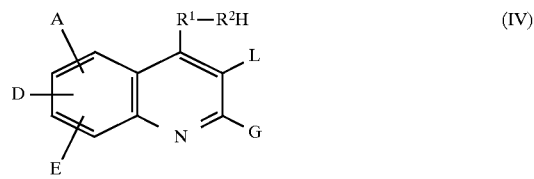

in which

A, D, E, G, L, R$^1$ and R$^2$ are as defined above, and these are then reacted with compounds of the general formula (IIa):

(IIa)

in which
A', D', E', G', L' and Y' are as defined for A, D, E, G, L and Y.

4. A composition for the treatment of degenerative diseases of the central nervous system which comprises a compound according to claim 1 and a biocompatible formulation aid.

5. A method for treating degenerative diseases of the central nervous system which comprises administering a therapeutically effective amount of a ring-bridged bis-quinolines of the formula (I)

(I)

in which
A, A', D, D', E, E', G, G', L and L' are identical or different and are hydrogen, cyclopropyl, cyclopentyl, cyclobutyl, cyclohexyl, phenyl, hydroxyl, fluorine, chlorine, trifluoromethyl, nitro, linear or branched alkyl or alkoxy, each of which has up to 4 carbon atoms, or a group of the formula —(CO)$_a$—NR$^3$R$^4$,
wherein
a is the number 0 or 1
R$^3$ and R$^4$ are identical or different and are hydrogen or linear or branched alkyl having up to 4 carbon atoms,
R$^1$ and R$^2$ together are a radical of the formula -continued wherein
R$^5$ and R$^7$ are identical or different and are hydrogen, carboxyl, linear or branched alkyl, acyl or alkoxycarbonyl, each of which has up to 3 carbon atoms, or a group of the formula —(CO)$_c$—NR$^{10}$R$^{11}$ or —OR$^{12}$,
wherein
c is the number 0 or 1,
R$^{10}$ and R$^{11}$ are identical or different and are hydrogen, phenyl, cyclopentyl, cyclohexyl, carboxyl, hydroxyl, linear or branched acyl or alkoxycarbonyl, each of which has up to 3 carbon atoms, or linear or branched alkyl having up to 3 carbon atoms which is optionally substituted by hydroxyl or by linear or branched alkoxy, acyl or alkoxycarbonyl, each of which has up to 3 carbon atoms,
R$^{12}$ is hydrogen or linear or branched alkyl or acyl, each of which has up to 3 carbon atoms, or
R$^7$ is linear or branched alkyl having up to 3 carbon atoms which is substituted by a group of the formula —OR$^{13}$, —O—CO—NR$^{14}$R$^{15}$ or —NR$^{16}$R$^{17}$,
wherein
R$^{13}$ is as defined above for R$^{12}$ and is identical thereto or different therefrom
R$^{14}$, R$^{15}$, R$^{16}$ and R$^{17}$ are identical or different and are as defined above for R$^{10}$ and R$^{11}$,
R$^6$ is hydrogen or methyl,
b is the number 1, 2 or 3
R$^8$ and R$^9$ are hydrogen or
R$^8$ is hydrogen and
R$^9$ is as defined above for R$^5$ and R$^7$ and is identical thereto or different therefrom.

6. The method according to claim 5 wherein the degenerative disease is dementia.

* * * * *